United States Patent

Monsue

[11] Patent Number: 5,933,863
[45] Date of Patent: Aug. 10, 1999

[54] PROTECTOR BANDAGE

[76] Inventor: Clyde Reece Monsue, 245 Pate Ln., Dickson, Tenn. 37055

[21] Appl. No.: 08/682,128

[22] Filed: Jul. 17, 1996

[51] Int. Cl.⁶ .................................................. A41D 19/00
[52] U.S. Cl. ............................ 2/21; 602/20; 2/163; 2/159
[58] Field of Search ................................. 2/21, 162, 163, 2/167, 169; 602/20–22

[56] References Cited

U.S. PATENT DOCUMENTS

| | | | |
|---|---|---|---|
| 1,231,194 | 6/1917 | Prince | 2/21 |
| 1,642,311 | 9/1927 | Richardson | 2/163 |
| 2,461,872 | 2/1949 | Beatty | 2/21 |
| 2,461,970 | 2/1949 | Finegan | 2/21 |
| 2,637,031 | 5/1953 | Friedman | 2/21 |
| 2,712,313 | 7/1955 | Levy | 2/21 |
| 2,827,635 | 3/1958 | Rasmus | 2/21 |
| 3,593,339 | 7/1971 | Main | 2/21 |
| 4,733,410 | 3/1988 | Glotkin | 2/21 |
| 5,228,142 | 7/1993 | Yoswein-McGreen | 2/21 |
| 5,497,510 | 3/1996 | Knowles et al. | 2/21 |

*Primary Examiner*—Gloria Hale
*Attorney, Agent, or Firm*—Waddey & Patterson; Lucian Wayne Beavers

[57] ABSTRACT

This bandage is used alone to protect the thumb, fingers or to be used over other bandages and act as a cover for them to keep them clean and help hold the bandage securely in place without the use of tape or clamps. Also to help prevent a person from further injury by hitting the uncovered injured thumb or finger. It makes the injured thumb or finger more comfortable as it conforms to the shape of the finger or thumb. It can be used over thumb, finger, guards, splints, etc.

8 Claims, 3 Drawing Sheets

PROTECTOR BANDAGE

BACKGROUND OF THE INVENTION

The present invention relates generally to hand bandages, and more specifically to a bandage for protecting the thumb or a finger of the wearer's hand. The protector bandage serves to protect a digit on the wearer's hand while the digit is healing from surgeries, injuries, breaks, or similar problems.

Bandages are often required to protect a person's hand while it is healing. It is a common occurrence, however, for a bandage to inadvertently come off of the finger when the bandage loses its adhesiveness to the skin. This is especially common in bigger bandages and bandages that cover areas that are in frequent motion, such as a finger or a thumb. Additionally, larger bandages often require the use of tape or clamps to keep the bandages in a constant position, which adds to the bulkiness and uncomfortability of the bandage.

Previous designs have attempted to solve the problems associated with bulky bandages with minimal success. U.S. Pat. No. 2,712,313 issued to Levy describes a surgical dressing that is used for an injured finger. The design taught by Levy allows a person to insert their finger into a tube with a string extending from one end of the tube. Therefore, the person must tie the string around the hand having the injured finger or the actual finger itself in order to secure the bandage to the finger. Such a design is difficult for the wearer to apply since the wearer will typically only have one hand to tie and secure the dressing to the finger.

U.S. Pat. No. 3,593,339 issued to Maine, et al. describes a draftsman's glove. The design in the Maine patent is for a glove that covers a draftsman's little finger so as to prevent lead and ink from getting on the draftsman's hand and to reduce the amount of lead or ink smearing or dirtying the paper. The glove has a seam across the wearer's little finger and the glove extends from below the tip of the little finger to the wrist of the wearer, with a tapered side going from the little finger across the palm of the hand to the opposite side of the wrist. This design is specifically created for use with a little finger, and it is bulky around the palm of the wearer's hand. The nontapered side extends all the way to the wearer's wrist, and the tapered side extends across the palm to the other side of the wrist. This design would not be allowed in use with any digit other than the little finger.

U.S. Pat. No. 2,827,635 issued to Rasmus describes a thumb protector for a bowler. This design provides for a covering that encircles the length of the wearer's thumb while allowing the top of the thumb to be open. This covering is further secured around the thumb with a strap that is attached to the base of the protector. This design is similar to the design described in the Levy patent, and is difficult for the user to apply because it requires the user to tie two straps around one wrist, therefore only allowing the use of one hand.

U.S. Pat. No. 5,497,510 issued to Knowles, et al. describes a thumb protector for fishing. This thumb protector provides a padded surface with an elastic backing to allow the wearer to engage a fish's mouth and the sharp teeth therein. The base of the thumb covering is attached to a strip of cloth that surrounds the wrist to secure the protector to the thumb. The ends of the cloth have patches of Velcro attached to them to thereby secure the thumb covering to the wearer's hand. Such a design is easier to attach to the hand than the designs described in the Levy and Knowles patents, but the design requires the added elements of velcro and may still be difficult for a person to apply with only one hand available.

What is needed, and not found in the prior art, is a protector bandage that is comfortable for the user, that is easy to place on the user's hand, digits, and any other guards or splints surrounding the digit, and that keeps any pre-existing bandages securely located by the injured digit.

SUMMARY OF THE INVENTION

The present invention for an improved protector bandage for use on a wearer's thumb or finger is disclosed. Accordingly, one of the objects of the invention is to provide a protector bandage that is easily placed on the wearer's hand, and stays in a constant position on the wearer's hand.

Another object of the invention is to provide a protector bandage for a wearer which provides a constant pressure to the bandage so that it stays placed on the wearer's finger.

Another object of the present invention is to provide a protector bandage that wraps around the wearer's wrist to stay positioned until the wearer removes the protector bandage. Other objects, features, and advantages will be readily apparent to those skilled in the art upon a reading of the following disclosure when taken in conjunction with the accompanying drawings.

DESCRIPTION OF THE PREFERRED EMBODIMENTS

Figure 1:
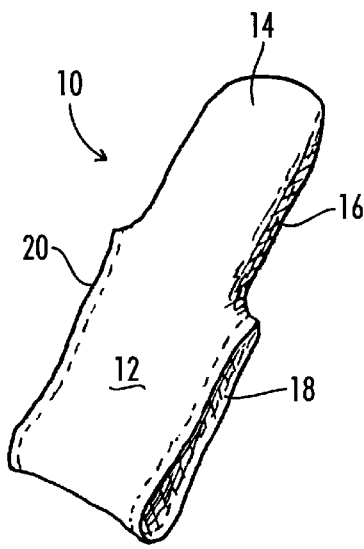
FIG. 1 is a perspective view of the protector bandage of the present invention, showing the wrist end portion and the tubular closed end digit pocket.
Figure 2:
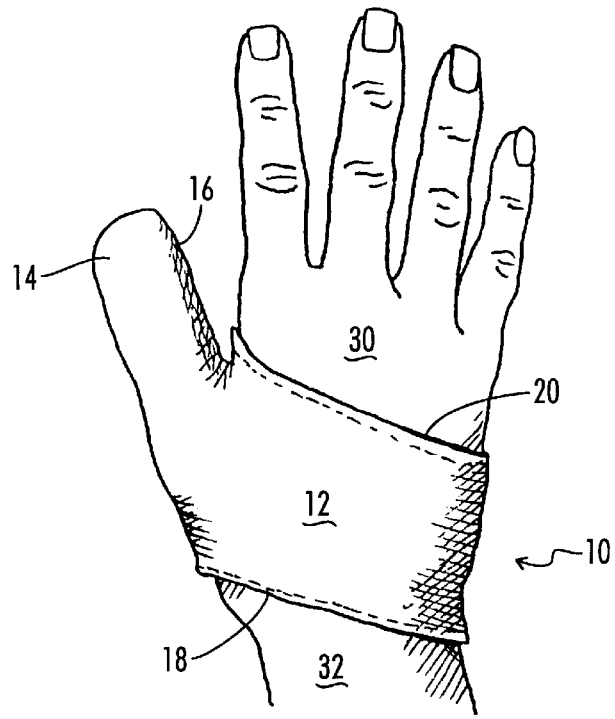
FIG. 2 is a perspective view of the back of a person's hand inserted into the protector bandage shown in FIG. 1, with the view showing the protector bandage covering the person's thumb.
Figure 3:
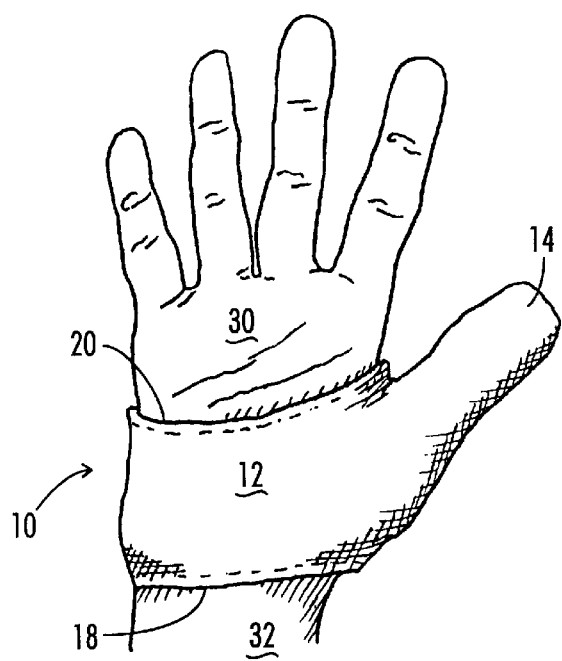
FIG. 3 is a perspective view of the palm of a person's hand inserted into the protector bandage shown in FIG. 1, with the view showing the protector bandage covering the person's thumb.

Referring to FIG. 1 of the drawings, a perspective view of the protector bandage 10 is shown. The protector bandage 10 includes two main sections: a circumferential wrist band portion 12 and a tubular, closed-end digit pocket 14. The wrist band portion 12 includes a strip of material that has a continuous single width. The wrist band portion 12 is further defined by an uppermost edge 20 and a lowermost edge 18. The digit pocket 14 is integrally connected to one end of the wrist band portion 12 between the uppermost edge 20 and the lowermost edge 18. This construction makes the protector bandage 10 a simple invention that requires only one piece of material.

The wrist band portion 12 is designed ergonomically to fit the hand 30 and wrist 32 of an individual. During application, the user inserts the digits of the hand 30 through the lowermost edge 18 of the wrist band portion 12 of the protector bandage 10. The digits then pass through the uppermost edge 20, and the digit to be protected is inserted into the digit pocket 14 of the protector bandage 10. The wrist band portion 12 is then adjusted around the wrist 32 of the user to allow for the utmost comfortability. The uppermost edge 20 is longer than the lowermost edge 18, which means that the lowermost edge 18 will provide a tighter fit around the wrist 32 of the user, whereas the uppermost edge 20 allows comfortable fit around the palm of the user's hand 30.

Once placed on the wearer's hand 30, the wrist band portion 12 has an upper end extending to the first digit joint of the wearer's hand 30 and a lower end extending across and around the wrist 32 of the wearer (shown in FIGS. 2–6). The digit pocket 14 is constructed to conform to the size of the digit of the hand 30 of the wearer. The digit pocket 14 can be fitted for the thumb (see FIGS. 2 and 3), the index finger, the middle finger, the ring finger (see FIGS. 4 and 5), or the little finger (see FIG. 6).

The protector bandage 10 is preferably made of a relatively flexible and elastic material. Such material allows the wearer to easily insert the wrist band portion 12 over the hand 30 and insert the finger into the tubular closed end portion 14 of the protector bandage 10. Additionally, the flexible material provides a constant force around the thumb or finger, which provides the bandage with a constant force to stay on the finger in the area desired.

Figure 4:
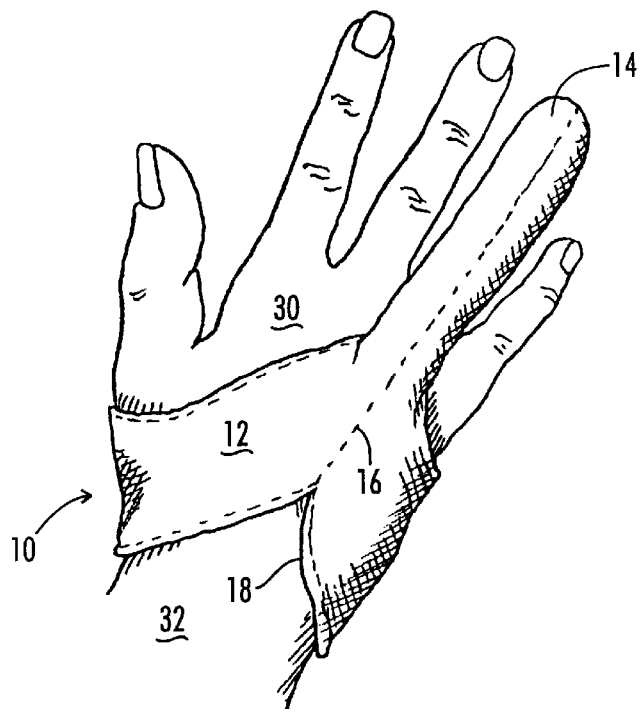
FIG. 4 is a perspective view of the back of a person's hand inserted into the protector bandage shown in FIG. 1, with the view showing the protector bandage covering the ring finger of the person's hand.
Figure 5:
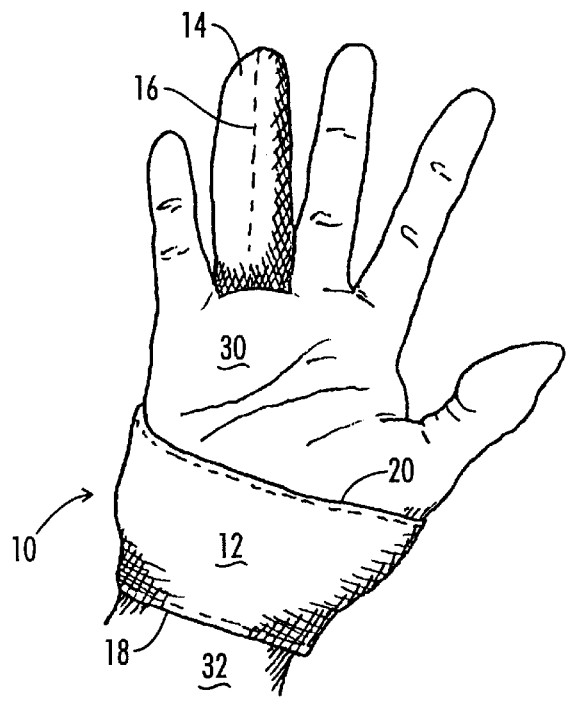
FIG. 5 is a perspective view of the palm of a person's hand inserted into the protector bandage shown in FIG. 1, with the view showing the protector bandage covering the ring finger of the person's hand.
Figure 6:
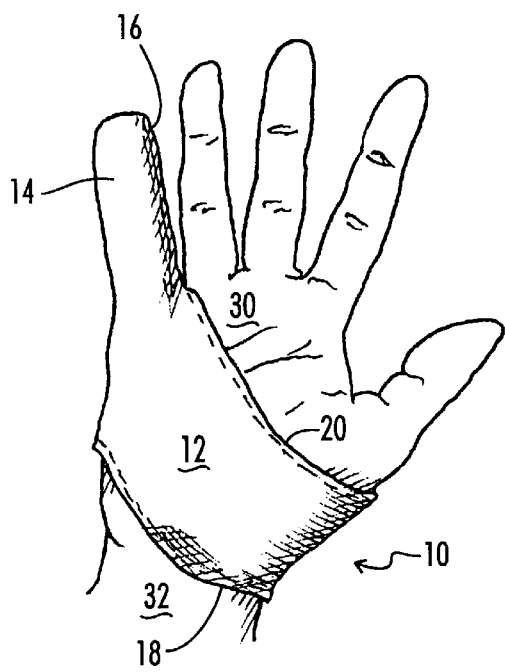
FIG. 6 is a perspective view of the palm of a person's hand inserted into the protector bandage shown in FIG. 1, with the view showing the protector bandage covering the little finger of the person's hand.

The protector bandage 10 also has a seam 16 crossing over the digit pocket 14 that extends from the lower end of the wrist band portion 12, around the digit, and over to an upper part of the wrist band portion 12 at the intersection of the digit and the hand 30 (see FIGS. 4 and 5). The seam 16 is sewn on the protector bandage 10 to allow the digit pocket 14 to provide the most tense connection with the digit of the hand 30 while preventing any displacement of the material around the surface of the digit and the hand 30. This seam 16 also eliminates unnecessary bulkiness in the palm of the hand 30. As seen in FIG. 5, the position of the seam 16 on the lowermost edge 18 allows for stretching either across the palm or the back of the user's hand 30 and around the wrist 32 without completely encircling the wrist 32.

Figure 7:
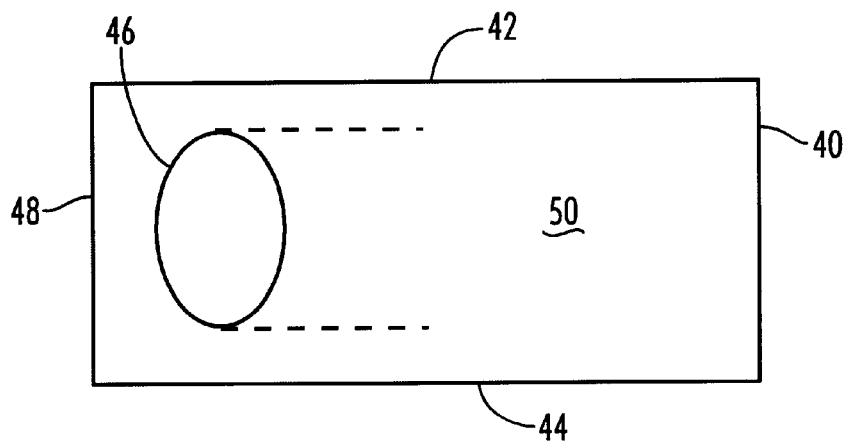
FIG. 7 is a top view of a strip of material to be transformed into a protector bandage.

A further advantage of the protector bandage 10 is the ease in which one is constructed. Only one piece of material is required to create this design. An example of one way to construct the protector bandage 10 is through the following steps. Referring to FIG. 7, a strip of elastic material 50 that is approximately 13.5 inches long and is approximately 2 inches wide is used to form the protector bandage 10 (these measurements allows a seam that is 0.25 inches deep for sewing and trimming of the material). The material 50 is then folded lengthwise in half to form a piece that is approximately 6.75 inches long. Starting approximately three inches from the folded side 40 of the material 50, the edges are sewn away from the folded side 40 towards the open side 48 to create the digit pocket 14. Further, a pattern 46 in the shape of the digit can be followed on the open side 48. To create the digit pocket 14, the pattern 46 should be the same contour as that of the digit which is to be covered by the digit pocket 14.

Figure 8A:
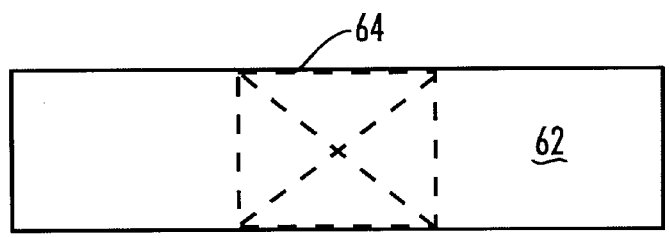
FIG. 8a is a top view of a piece of material to become the wrist band portion of the protector bandage.
Figure 8B:
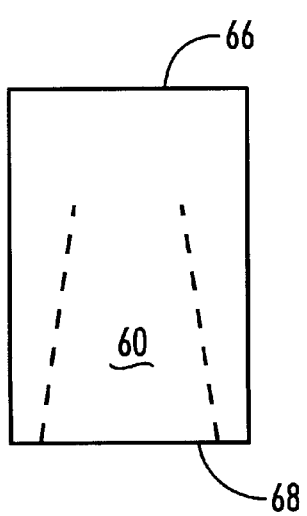
FIG. 8b is a top view of a piece of material to become a closed end digit pocket of the protector bandage.
Figure 8C:
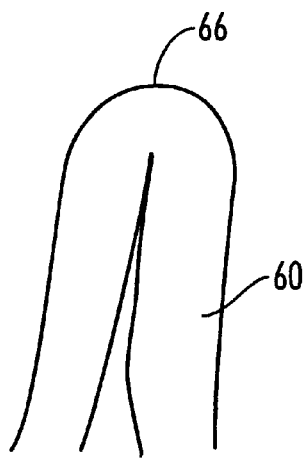
FIG. 8c is a side view of the piece of material of FIG. 8b, the view showing the fold in the material.

Another example for creating the protector bandage 10 using two pieces of material provides for a better fit for the index, middle, and ring fingers of the hand 30. This design is shown in FIGS. 8a–8c. The two pieces of material required are a first piece 62 (shown in FIG. 8a) being approximately 6.25 inches long and two inches wide (for the wrist band portion 12) and a second piece 60 (shown in FIGS. 8b and 8c) being approximately 7.25 inches long and four inches wide (for the finger pocket 14).

The first step in making this protector bandage 10 is to fold the four inch piece 60 of material 0.5 inches on both sides and hem 3.5 inches from the bottom side 68 towards the top end (not shown). After folding the four inch piece 60 of material in half lengthwise (shown in FIG. 8b), it must be sewn again, starting at the top end and going across and down 2.5 inches, rounding and shaping as a finger.

Next, the first piece 62 is laid on a flat surface, and the second piece 60 is centered in the middle of the first piece 62. With the bottom ends of both the first and second pieces 62, 60 flush, the second piece 60 is sewed to the first piece 62. A box design 64 is used to sew the first piece 62 with the second 60 (see FIG. 8a). An X shape 70 is then sewn in the box 64 from corner to corner to reinforce the connection.

Thus, although there have been described particular embodiments of the present invention of a new and useful Protector bandage, it is not intended that such references be construed as limitations upon the scope of this invention except as set forth in the following claims.

I claim:

1. A protector bandage for protecting a digit on a wearer's hand, the protector bandage comprising:

a circumferential wrist band portion having a constant width and comprised of an elastic material;

said wrist band portion having an upper end extending to the wearer's digit joint and a lower end extending across and around the wrist of the wearer; and a tubular closed-end digit pocket, constructed to conform to the digit of a wearer, said digit pocket integrally attached to said wrist band portion.

2. The protector bandage of claim 1, the wrist band portion further having an uppermost edge and a lowermost edge.

3. The protector bandage of claim 2, said uppermost edge being longer than said lowermost edge.

4. The protector bandage of claim 2, the protector bandage further comprising a seam extending from said lowermost edge of said wrist band portion, around the digit, to said uppermost edge of said wrist band portion at the digit and hand intersection.

5. A method of constructing a protector bandage for protecting a digit including the steps of:

obtaining a strip of elastic material;

folding said strip of elastic material in half thereby providing a first and second side edge, a folded edge, and an open end;

sewing away from said folded edge of the strip of elastic material along said first edge towards said open end starting at a distance away from said folded edge;

sewing a rounded edge to conform to the shape of the digit on the open end of said strip of elastic material; and sewing down along said second edge of said strip of elastic material to provide a wrist opening adjacent the closed end.

6. A method of constructing a protector bandage for protecting a wearer's digit and hand including the steps of:

obtaining a wrist band of elastic material;

obtaining a length of elastic material that is twice the length of the wearer's digit from the top of the digit to the digit/hand joint;

folding said length of material in half forming a closed top end;

opening left and right edges and a bottom opening end as a digit pocket;

sewing along both right and left edges of said digit pocket to close said right and left side edges; and attaching the open end of said digit pocket to said wrist band.

7. A method of protecting a digit of a wearer's hand with a protector bandage, the method comprising:

A. inserting the digit into a digit pocket;

B. moving a wrist band portion connected to said digit pocket over the wearer's hand; and C. securing said elastic wrist band around the base of the wearer's hand to fix said digit pocket around the digit.

8. The method of claim 7 wherein step B precedes step A.

* * * * *